United States Patent
Boday et al.

(10) Patent No.: US 10,702,610 B2
(45) Date of Patent: Jul. 7, 2020

(54) METHOD OF MAKING SULFUR-CONTAINING POLYMERS FROM HEXAHYDROTRIAZINE AND DITHIOL PRECURSORS

(71) Applicants: International Business Machines Corporation, Armonk, NY (US); AGENCY FOR SCIENCE, TECHNOLOGY AND RESEARCH, Singapore (SG)

(72) Inventors: Dylan J. Boday, San Jose, CA (US); Willy Chin, Singapore (SG); Jeannette M. Garcia, San Jose, CA (US); James L. Hedrick, San Jose, CA (US); Xiyu Ke, Singapore (SG); Rudy J. Wojtecki, San Jose, CA (US); Yi Yan Yang, Singapore (SG)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/116,045

(22) Filed: Aug. 29, 2018

(65) Prior Publication Data

US 2018/0369397 A1 Dec. 27, 2018

Related U.S. Application Data

(63) Continuation of application No. 14/830,251, filed on Aug. 19, 2015, now Pat. No. 10,080,806.

(51) Int. Cl.
| | |
|---|---|
| A61K 47/20 | (2006.01) |
| C08G 75/02 | (2016.01) |
| A61K 47/59 | (2017.01) |
| C08G 65/48 | (2006.01) |
| A61K 31/7105 | (2006.01) |
| A61K 38/08 | (2019.01) |
| A61K 31/795 | (2006.01) |

(52) U.S. Cl.
CPC .......... *A61K 47/59* (2017.08); *A61K 31/7105* (2013.01); *A61K 31/795* (2013.01); *A61K 38/08* (2013.01); *C08G 65/48* (2013.01); *C08G 75/02* (2013.01)

(58) Field of Classification Search
None
See application file for complete search history.

(56) References Cited

U.S. PATENT DOCUMENTS

| | | |
|---|---|---|
| 2,191,753 A | 2/1940 | Coffman et al. |
| 2,889,277 A | 6/1959 | Hughes |
| 3,173,799 A | 3/1965 | George |
| 3,314,927 A | 4/1967 | Kelley |
| 3,340,232 A | 9/1967 | Smith et al. |
| 3,444,145 A | 5/1969 | Youngman et al. |
| 3,598,748 A | 8/1971 | Hirosawa |
| 3,939,119 A | 2/1976 | O'Shea |
| 3,957,742 A | 5/1976 | Kveton |
| 4,010,028 A | 3/1977 | Irwin, Sr. et al. |
| 4,086,211 A | 4/1978 | Nakauchi et al. |
| 4,106,904 A | 8/1978 | Oude Alink et al. |
| 4,224,417 A | 9/1980 | Hajek et al. |
| 4,225,481 A | 9/1980 | Wagner |
| 4,246,160 A | 1/1981 | Wagner et al. |
| 4,280,004 A | 7/1981 | Jeblick et al. |
| 4,301,262 A | 11/1981 | Wagner et al. |
| 4,654,410 A | 3/1987 | Kashiwame et al. |
| 4,839,460 A | 6/1989 | Molzahn |
| 4,874,858 A | 10/1989 | Magistro |

(Continued)

FOREIGN PATENT DOCUMENTS

| | | |
|---|---|---|
| CH | 0473542 A | 6/1969 |
| CN | 101265255 A | 9/2008 |

(Continued)

OTHER PUBLICATIONS

D.R. Anderson et al., Thermally resistance polymers containing the S-friazine ring, Journal of Polymer Science Part A-1: PolymerO;emistry, vol. 4, Issue 7, pp. 1689-1702 [Abstract Only].

(Continued)

*Primary Examiner* — Kevin S Orwig
(74) *Attorney, Agent, or Firm* — Patterson + Sheridan, LLP (57) ABSTRACT

Polythioaminal polymers are made from hexahydrotriazine precursors and dithiol precursors. The precursors are blended together and subjected to mild heating to make the polymers. The polymers have the general structure

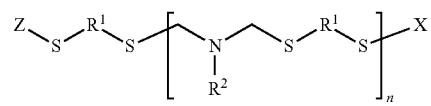

wherein each $R^1$ is independently an organic or heteroorganic group, each $R^2$ is independently a substituent having molecular weight no more than about 120 Daltons, X and Z are each a sulfur-bonded species, at least one of X and Z is not hydrogen, and n is an integer greater than or equal to 1. X and Z may be hydrogen or a functional group, such as a thiol-reactive group. The reactive thiol groups of the polythioaminal may be used to attach thiol-reactive end capping species. By using water soluble or water degradable dithiols, such as polyether dithiols, water soluble polythioaminals may be made. Some such polymers may be used to deliver therapeutics with non-toxic aqueous degradation products.

17 Claims, 4 Drawing Sheets

(56) References Cited

U.S. PATENT DOCUMENTS

| | | |
|---|---|---|
| 4,877,451 A | 10/1989 | Winnik et al. |
| 5,112,796 A | 5/1992 | Iannicelli |
| 5,149,768 A | 9/1992 | White et al. |
| 5,336,807 A | 8/1994 | Burgoyne, Jr. et al. |
| 5,354,453 A | 10/1994 | Bhatia |
| 5,360,876 A | 11/1994 | Burgoyne, Jr. et al. |
| 5,554,349 A | 9/1996 | Rivers et al. |
| 5,674,377 A | 10/1997 | Sullivan, III et al. |
| 5,693,747 A | 12/1997 | Deisenroth et al. |
| 5,795,560 A | 8/1998 | Reed |
| 5,830,243 A | 11/1998 | Wolak et al. |
| 5,840,823 A | 11/1998 | Licht et al. |
| 5,958,352 A | 9/1999 | Callaway et al. |
| 6,132,933 A | 10/2000 | Nguyen |
| 6,419,945 B1 | 7/2002 | Gresser et al. |
| 6,541,181 B1 | 4/2003 | Levanon et al. |
| 6,566,035 B1 | 5/2003 | Aoshima |
| 6,641,978 B1 | 11/2003 | Chapman et al. |
| 6,663,841 B2 | 12/2003 | Salma et al. |
| 6,911,300 B2 | 6/2005 | Sato et al. |
| 7,045,579 B2 | 5/2006 | Van Den Berg et al. |
| 7,384,434 B2 | 6/2008 | Malfer et al. |
| 7,652,119 B2 | 1/2010 | Wakabayashi et al. |
| 7,989,146 B2 | 8/2011 | Burberry et al. |
| 8,389,205 B2 | 3/2013 | Duerig et al. |
| 8,450,043 B2 | 5/2013 | Coady et al. |
| 8,562,964 B2 | 10/2013 | Ljubimova et al. |
| 8,574,815 B2 | 11/2013 | Coady et al. |
| 8,632,947 B2 | 1/2014 | Bentley et al. |
| 9,120,897 B1 | 9/2015 | Boday et al. |
| 9,120,899 B1 | 9/2015 | Boday et al. |
| 9,139,698 B1 | 9/2015 | Boday et al. |
| 9,206,289 B1 | 12/2015 | Boday et al. |
| 9,228,059 B2 | 1/2016 | Boday et al. |
| 9,388,281 B2 | 7/2016 | Boday et al. |
| 9,534,084 B1 | 1/2017 | Boday et al. |
| 9,550,863 B1 | 1/2017 | Boday et al. |
| 9,631,119 B1 | 4/2017 | Boday et al. |
| 9,637,661 B1 | 5/2017 | Boday et al. |
| 9,765,188 B2 | 9/2017 | Boday et al. |
| 9,862,802 B2 | 1/2018 | Boday et al. |
| 9,879,118 B2 | 1/2018 | Boday et al. |
| 10,080,806 B2 | 9/2018 | Boday et al. |
| 10,113,034 B2 | 10/2018 | Boday et al. |
| 2002/0063096 A1 | 5/2002 | Ohtani |
| 2002/0115791 A1 | 8/2002 | Duncan et al. |
| 2003/0039689 A1 | 2/2003 | Chen et al. |
| 2003/0224222 A1 | 12/2003 | Matsuoka et al. |
| 2004/0060405 A1 | 4/2004 | Kao |
| 2006/0275337 A1 | 12/2006 | Cohen Stuart et al. |
| 2007/0077511 A1 | 4/2007 | Tredwell et al. |
| 2008/0199810 A1 | 8/2008 | Narang et al. |
| 2009/0039018 A1 | 2/2009 | Jordi et al. |
| 2009/0250659 A1 | 10/2009 | Gatlin |
| 2010/0048756 A1 | 2/2010 | Loccufier et al. |
| 2010/0107476 A1 | 5/2010 | Cosimbescu |
| 2011/0271096 A1 | 11/2011 | Bharrat et al. |
| 2012/0049308 A1 | 3/2012 | Nishimura et al. |
| 2012/0232328 A1 | 9/2012 | Gwenin et al. |
| 2013/0004454 A1 | 1/2013 | Weiss et al. |
| 2013/0118996 A1 | 5/2013 | Kaplan |
| 2013/0181161 A1 | 7/2013 | Pajel et al. |
| 2014/0013425 A1 | 1/2014 | Samson |
| 2014/0031500 A1 | 1/2014 | Matsumura et al. |
| 2015/0141293 A1 | 5/2015 | Williges et al. |
| 2015/0344461 A1 | 12/2015 | Zhang |
| 2015/0344629 A1 | 12/2015 | Boday |
| 2015/0344633 A1 | 12/2015 | Boday |
| 2017/0049902 A1 | 2/2017 | Hedrick et al. |
| 2017/0096532 A1 | 4/2017 | Boday et al. |

FOREIGN PATENT DOCUMENTS

| | | |
|---|---|---|
| CN | 101343421 A | 1/2009 |
| CN | 103101899 A | 5/2013 |
| CN | 103483486 A | 1/2014 |
| EP | 473542 A1 | 3/1992 |
| EP | 2636697 A1 | 9/2013 |
| GB | 535577 A | 4/1941 |
| GB | 928112 A | 6/1963 |
| GB | 942932 A | 11/1963 |
| GB | 1531578 A | 11/1978 |
| JP | 2000319396 A | 11/2000 |
| JP | 2006516548 A | 7/2006 |
| JP | 2006519766 A | 8/2006 |
| WO | 0166614 A2 | 9/2001 |
| WO | 0198388 A1 | 12/2001 |
| WO | 0226849 A1 | 4/2002 |
| WO | 2004060405 A2 | 7/2004 |
| WO | 2014179100 A1 | 11/2014 |

OTHER PUBLICATIONS

Ekinci et al., "Preparation, Characterization and H202 Selectivity of Hyperbranched Polyimides Containing Triazine", Journal of Polymer Research, 2005, pp. 205-210.

Elbert, et al. "Conjugate Addition Reactions Combined with Free-Radical Cross-Linking for the Design of Materials or Tissue Engineering," Biomacromolecules 2001, 2. 430-441; Published on Web Mar. 3, 2001 [Abstract Only].

Fabin Suriano et al. Functionalized cyclic carbonates: from synthesis and metal-free catalyzed ring-opening polymerization to applications, Polymer Chemistry, The Royal Society of Chemistry, 2011, Received Jul. 6, 2010, Accepted Aug. 13, 2010, pp. 528-533.

Ferrar, "Reactions of Formaldehyde With Aromatic Amines," J. Appl. Chem, 14, 1964, 389-399. [Abstract Only].

Go Saito et al.,"Drug delivery strategy utilizing conjugation via reversible disulfide linnkages: role and site of cellular reducing activites," Advanced Drug Delivery Reviews 55, (2003) 199-215.

Gavin O. Jones, "Computational and Experimental Studies on the Mechanism of Formation of Poly(hexahydrotriazine)s and Poly(hemiaminal)s from the Reactions of Amines with Formaldehyde," Organic Letters, 2014, vol. 16, 5502-5505.

Geng, et al., "Nanoindentation behavior of ultrathin polymeric films," Polymer 46 (2005) 11768-11772; Available online Oct. 19, 2005.

Hemant S. Patel et al., Studies on Synthesis and Characterization of some Novel Aromatic Copolyesters based on s-Triazine, Iranian Polymer Journal, vol. 14, No. 12, 2005, pp. 1090-1098.

Hiller, et al., "Laser-engraveable hexahydrotriazine polymer networks," Mat Res Innovat (2002) 6: 179-184. [Abstract Only].

Hydrogen Sulfide Management. Mitigation options in petroleum refining, storage and transportation, White Paper, Baker Hughes, pp. 1-12.

Jeannette M. Garcia et al., "Recyclable, Strong Thermosets and Organogels via Paraformaldehyde Condensation with Diamines," Science, 344, 732 (2014).

John Markoff, Error at IBM Lap Finds New Famiiy of Materials, New York Times, May 15, 2014, 4 pages.

Katrin Knop et al., "Poly(ethylene glycol) in Drug Delivery: Pros and Cons as Well as Potential Alternatives," Angew. Chem. Int. Ed. 2010, 49, 6288-6308.

Oliver, et al. "Measurement of hardness and elastic modulus by; instrumented indentation: Advances in understanding and; refinements to methodology," J. Mater. Res. vol. 19, No. 1, Jan. 3-20, 2004.

Rakhimova et al. "Effective synthesis of N-aryl-substituted 1,5,3-dithiazepinanes and 1,5,3-dithiazocinanes". Chem. Hetero. Compo., vol. 48(7) pp. 1050-1058 (Jul. 2012).

Raquel Lebrero et al. Odor abatement in biotrickling filters: Effect of the EBRT on methyl mercaptan and hydrophobic VOCs removal, Bioresource Technology, Special Issue: Innovative Researches on Algal Biomas. vol. 109, Apr. 2012, pp. 38-45.

Rudy Wojtecki et al., "Using the dynamic bond to acceess macroscopically responsive structurally dynamic polymers," Natural Materials, vol. 10, Jan. 2011, 14 pages.

Singh, et al., "Ultrasound mediated Green Synthesis of Hexa-hydro Triazines," J. Mater. Environ. Sci. 2 (4) (2011) 403-406.

(56) References Cited

OTHER PUBLICATIONS

Stafford, et al., "A buckling-based metrology for measuring; the elastic moduli of polymeric thin films," Nature Materials. sub.—Aug. 3, 2004, 545-550;Published online: Jul. 11, 2004.

Stuart Rowan et al.,"Dynamic Covalent Chemistry," Angew. Chem. Int. Ed. 2002, 41, 898-952.

Wang Yulan et al., Synthesis and Properties of Poly-1, 3, 5-Triazines, Polymer Communications, No. 2, '1984, pp. 117-123 (abstract only).

Zhu et al., "Synthesis of novel nitrogen- and sulfur-containing conjugated polymers used as hole-transporting materials or organic light-emitting diodes," Journal of Polymer Science Part A; vol. 40, Issue 9, May 1, 2002, pp. 1321-1333; FirstPublished Mar. 14, 2002; DOI: 10.1002/pola.10214, [Abstract Only].

Wojtecki et al. "Developments in Dynamic Covalent Chemistries from the Reaction of Thiols with Hexahydrotriazines" J. Am. Chem. Soc. 2015, 137 (45)14248-14251.

IBM, "List of IBM Patents or Patent Applications Treated as Related," for U.S. Appl. No. 16/116,045, filed Aug. 29, 2018.

METHOD OF MAKING SULFUR-CONTAINING POLYMERS FROM HEXAHYDROTRIAZINE AND DITHIOL PRECURSORS

CROSS-REFERENCE TO RELATED APPLICATIONS

This application is a continuation of co-pending U.S. patent application Ser. No. 14/830,251, filed Aug. 19, 2015. The aforementioned related patent application is herein incorporated by reference in its entirety.

This application contains a sequence listing submitted electronically via EFS-web, which serves as both the paper copy and the computer readable form (CRF) and consists of a file entitled ARC920150017 Sequence Listing_ST25.txt, which is incorporated by reference in its entirety.

The present invention relates to polythioaminals and the use of such polymers in the delivery of therapeutics.

BACKGROUND

By one measure, delivery of therapeutic medicaments generated $122.3 billion in 2012 and will grow to $198.4 billion by 2017. Growth in the market for drug delivery technology provides participants with opportunities to create new ways to deliver increasingly potent and specific therapeutics. Polyethylene glycol (PEG) remains the only synthetic polymer used in commercial products as a stealth drug delivery vehicle because it is substantially biocompatible, and it prolongs blood circulation times for therapeutic carriers. PEG is also associated with hazardous side-effects including immunological responses that can lead to increased blood clotting and embolism, nonspecific recognition by the immune system, and hypersensitivity reactions. These side-effects may be intensified by the non-biodegradability of PEG. Therefore, there is a need in the drug delivery industry for a versatile delivery vehicle for therapeutics that has fewer side-effects.

SUMMARY

Described herein is a polymer having the general structure wherein each $R^1$ is independently an organic or hetero-organic species, each $R^2$ is independently a substituent having a molecular weight no more than about 120 Daltons, X and Z are each a sulfur-bonded species, at least one of X and Z is not hydrogen, and n is an integer greater than or equal to 1.

Also described herein is a polymer comprising a repeating unit with the following structure:

and a segment with the following structure:

wherein $R^1$ is an organic or hetero-organic species, $R^2$ is a substituent having a molecular weight no more than about 120 Daltons, X is a linking group covalently bonded to a sulfur atom, and K is any radical suitable for bonding to X.

Also described herein is a method of forming a material, comprising: mixing an N-substituted hexahydrotriazine with a dithiol to form a first mixture; and heating the first mixture to form a polythioaminal polymer, wherein the substituent bonded to one or more of the nitrogen atoms of the N-substituted hexahydrotriazine forms a hydride that is volatile at temperatures less than 200° C.

BRIEF DESCRIPTION OF THE FIGURES AND DRAWINGS

So that the manner in which the above recited features of the present disclosure can be understood in detail, a more particular description of the disclosure, briefly summarized above, may be had by reference to embodiments, some of which are illustrated in the appended drawings and in the body of the specification. It is to be noted, however, that the appended and embedded drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures and drawings. It is contemplated that elements disclosed in one embodiment may be beneficially utilized on other embodiments without specific recitation.

DETAILED DESCRIPTION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Similarly, the terms "further comprises," "may further comprise," and "further comprising," when used in this specification, specify the presence of additional features or components, without precluding the presence or addition of other features or components. The terms "further comprises," "may further comprise", and "further comprising" in this specification do not mean that any features or components are excluded from any embodiments. When a range is used to express a possible value using two numerical limits a and b (e.g., a concentration of a ppm to b ppm), unless otherwise stated the value can be a, b, or any number between a and b.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

The inventors have made a new polymer having the general structure

This polymer (A) is a polythioaminal, which may be formed by reacting a hexahydrotriazine ("HT") with a thiol, according to the following general reaction scheme:

In this scheme, each instance of $R^1$ is independently an organic or hetero-organic group. In some cases, each instance of $R^1$ may be the same species. Each instance of $R^2$ is independently an organic or hetero-organic group that may have a molecular weight of not more than about 120 Daltons, and each instance of $R^2$ may be the same species. X and Z are each, independently, a sulfur-bonded species, and n is an integer greater than or equal to 1. In each instance, $R^1$ may be a hydrocarbon species, an aromatic and/or aliphatic; a polymer species such as polyethylene glycol, polyol species; or polyether species, any of which may have non-hydrogen substituents, as governed by the dithiols used in the reaction scheme. In one embodiment, at least one instance of $R^1$ is polyethylene glycol. In another embodiment, each instance of $R^1$ is the same species.

Alkane dithiols such as butane dithiol, pentane dithiol, and hexane dithiol may be used as precursors. Aromatic dithiols such as benzene dithiol, toluene dithiol, and xylene dithiol may also be used as precursors. The dithiol may be a polymer species, such as a dithiol-capped polyolefin. Dithio-polyol species may also be used, such as dithioalkane diols, triols, and the like. Each instance of $R^2$ may independently be hydrogen, fluorine, methyl, or an alkyl group such as ethyl, propyl, butyl, hexyl, or cyclohexyl.

Reaction scheme (1) begins with the following polymerization reaction:

In reaction (2), an HT is reacted with a dithiol, or a mixture of dithiols, to form a polythioaminal, with $R^1$ and $R^2$ as described above. The reaction may be performed in a solvent medium such as N-methyl pyrrolidone (NMP), or other suitable solvent, to control viscosity. An example of such reaction is the reaction between 1,3,5-trimethylhexahydrotriazine and hexanedithiol, as follows:

Reaction (3) may be performed using NMP as solvent, or using the reactants alone as solvent. For example, the reaction (3) may be performed in excess triazine up to about 2 equivalents, such as from 1.3 to 1.5 equivalents, for example about 1.3 equivalents. The precursors may be obtained from commercial suppliers such as Sigma-Aldrich, or may be synthesized.

Reaction (3) may be performed according to the following exemplary process. In a stirred vessel, the dithiol precursor is added to 1.3 equivalents of the triazine precursor. The vessel is purged with nitrogen or other inert gas and sealed, and the reaction mixture is heated to 85° C. The reaction mixture is maintained at 85° C. for 18 hours to form oligomers. Vacuum is then applied to the vessel to remove volatile byproducts, driving growth in molecular weight of the resulting polymer molecules according to LeChatelier's Principle. The reaction is allowed to proceed for 24 hours, during which stirring may cease due to viscosity of the mixture. The resulting polymer is typically optically transparent and may range from a solid to a viscous liquid.

Figure 1:
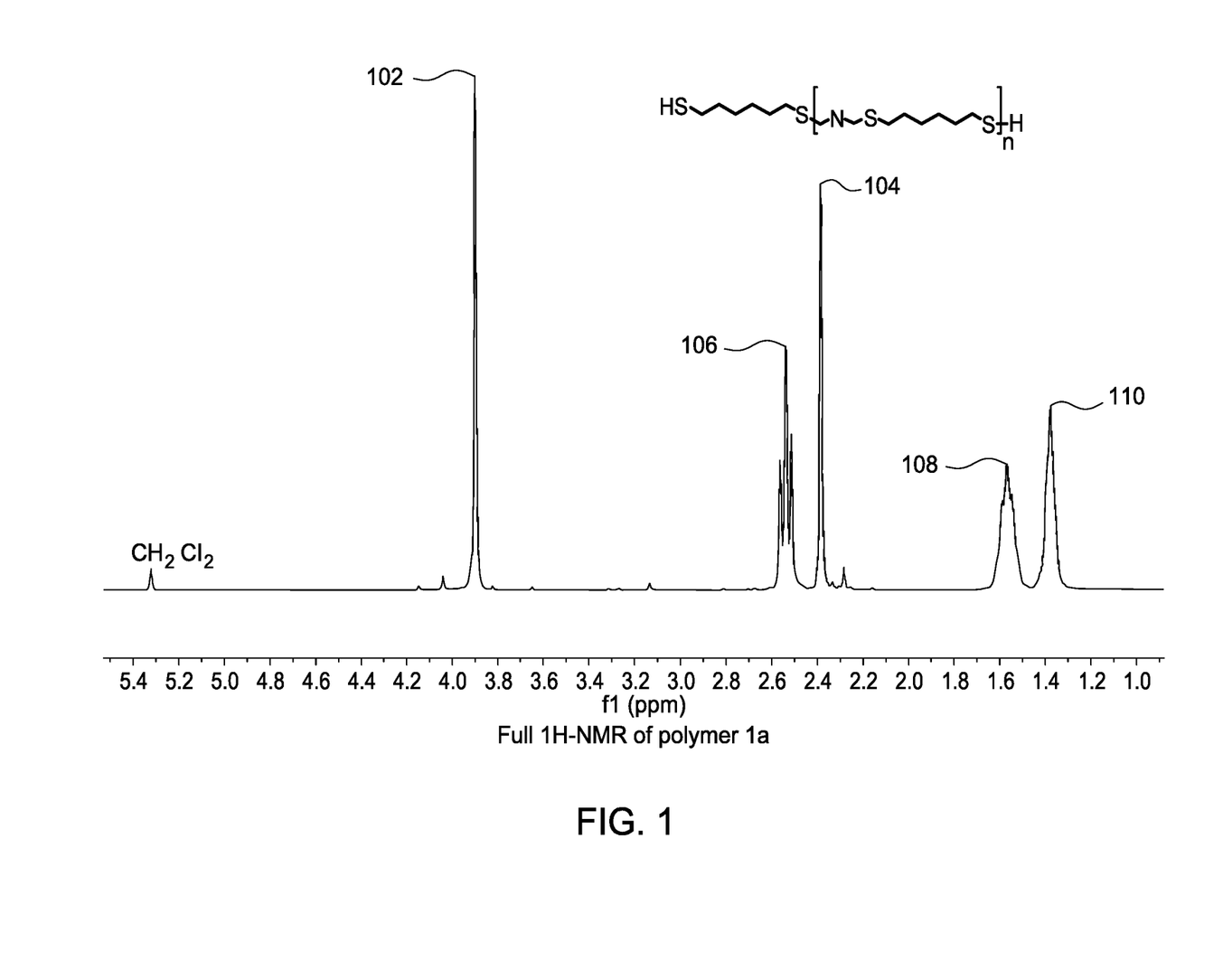
FIG. 1 is a 1H-NMR trace for an exemplary reaction of 1,3,5-trimethylhexahydrotriazine and hexanedithiol.

In one example of reaction (3), an NMR trace was obtained by the inventors. FIG. 1 is a 1H-NMR trace for an exemplary reaction of 1,3,5-trimethylhexahydrotriazine and hexanedithiol to form an embodiment of the polymer (A). The NMR trace of FIG. 1 was acquired in $CDCl_3$ using a Bruker 400-MHz NMR spectrometer. Chemical shifts in FIG. 1 are expressed in parts per million relative to TMS. Peak 102 indicates the carbon atom between a sulfur atom and a nitrogen atom. Peak 104 indicates the methyl group bonded to the nitrogen atom. Peak 106 indicates a carbon atom other than the carbon atom of peak 102 in the alpha position relative to a sulfur atom. Peak 108 indicates a carbon atom in the beta position relative to a sulfur atom. Peak 110 indicates the remaining carbon atoms between the carbon atoms of peak 106. The NMR trace of FIG. 1 is thus consistent with the polythioaminal product of reaction (3) above.

Figure 2:
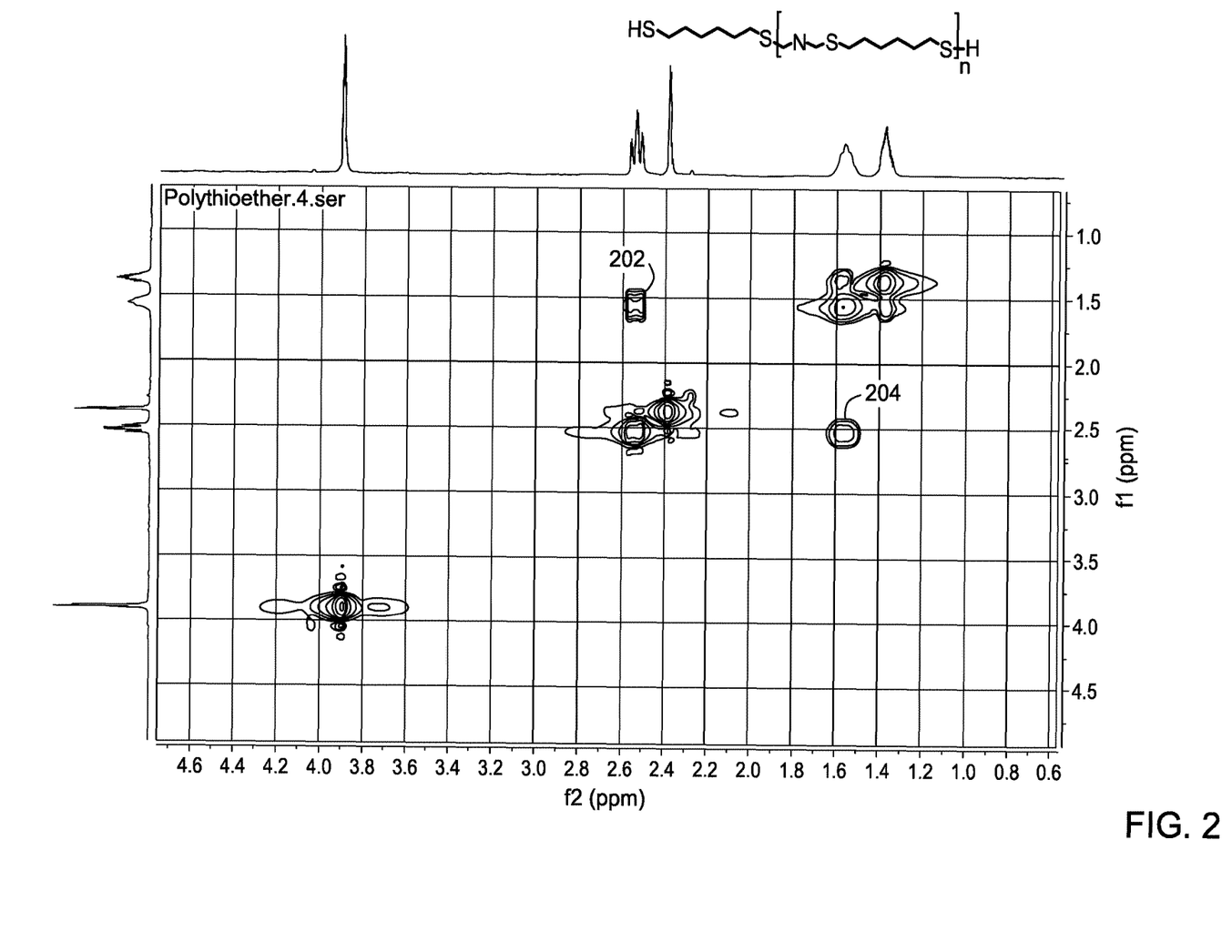
FIG. 2 is a 2-d COSY NMR of the product of FIG. 1.

FIG. 2 is a 2-d COSY NMR of the product of FIG. 1. Off-line energy aggregates 202 and 204 indicate interaction of protons at the positions of the carbon atoms of peaks 106 and 108 of FIG. 1, providing further evidence of the product of reaction (3).

Each instance of $R^2$ may be any group with the property that the hydride of $R^2$, $R^2$—H, is volatile at a temperature up to about 200° C., under vacuum if necessary. $R^2H$ is a by-product of reaction (2), and if $R^2$—H can be removed from the reaction mixture, polymer growth is enhanced. Table 1A shows the results of a series of reactions following the scheme of reaction (2) using various different precursors. Table 1B describes the various precursors in detail.

TABLE 1A

Reactions Forming Polymer
HS—$R^1$—S—[—CN($R^2$)CS—$R^1$—S—]$_n$—H

| Polymer | $M_w$ (g/mol) | $M_n$ (g/mol) | Polydispersity | $T_g$ (° C.) | Viscosity (Pa · sec) |
|---|---|---|---|---|---|
| 1a | 19,800 | 8,100 | 2.4 | −59.1 | 107.1 |
| 1b | 17,100 | 9,000 | 1.9 | −64.3 | 297.0 |
| 1c | 8,700 | 4,900 | 1.8 | −64.5 | 7.8 |
| 1d | 5,200 | 2,900 | 1.8 | −25.8 | 115.9 |
| 1e | ≤2,000 | ≤1,500 | — | — | — |
| 2a | 3,800 | 2,500 | 1.5 | 50.8 | — |
| 3a | 15,000 | 7,500 | 2.0 | −44.4 | 46.8 |
| 4a | 35,600 | 20,700 | 1.7 | −50.5 | — |

TABLE 1B

Precursors for Polymers of Table 1A

| Precursor | $R^1$ Structure | $R^2$ Structure | Precursor Name |
|---|---|---|---|
| 1 | (hexyl chain) | | hexanedithiol |
| 2 | (CH(OH)CH(OH)) | | Dithiothreitol (Cleland's Reagent) |
| 3 | ([CH₂CH₂O]₃) | | Tetraethylene glycol dithiol |
| 4 | ([CH₂CH₂O]$_n$) | | Polyethylene glycol dithiol |
| a | | (methyl) | 1,3,5-trimethylhexahydrotriazine |
| b | | (butyl) | 1,3,5-tributylhexahydrotriazine |
| c | | (hexyl) | 1,3,5-trihexylhexahydrotriazine |
| d | | (methylcyclohexyl) | 1,3,5-tris(methylcyclohexyl) hexahydrotriazine |
| e | | (paramethylaminophenyl) | 1,3,5-tris(paramethylaminophenyl) hexahydrotriazine |

Molecular weight averages for Table 1 were measured by size exclusion chromatography using a GPC system equipped with a Waters Corp.—717 auto sampler, 515 HPLC pump, 2410 Differential Refractometer, and Styragel High Resolution GPC column bank: Styragel HR1, HR2, HR4E, and HR5E. All GPCs were carried out using Omni-Solv® THF with flow rate of 1 mL/min. at ambient temperature. All molecular weight averages are relative to calibrations using Linear PS standards from Polymer Laboratories.

Molecular weight of the resulting polymer molecules is enhanced by volatility of substituents of the triazine precursor. Table 1 indicates that as molecular weight of the $R^2$ group increases from species a to species e, the developed average molecular weight (weight-average molecular weight $M_w$ and number-average molecular weight $M_n$) of the polymer decreases. It is believed this is due to volatility of the byproduct hydride $R^2$—H. If the byproduct cannot be easily removed, reaction kinetics are slowed by buildup of byproducts in the reaction mixture. Application of heat and vacuum improves results up to a point. Because the polymer itself begins to decompose at temperatures above about 200° C., additional heating is counter-productive. In one aspect, polymerization is enhanced using trazine substituents $R^2$ having a molecular weight less than about 120 Daltons. In another aspect, polymerization is enhanced using triazine substituents whose hydrides have room temperature vapor pressure of at least about 10 Torr.

As Table 1 shows, the polymers described herein may have a weight-average molecular weight $M_w$ as low as 3,800 Daltons and up to about 36,000 Daltons. In most embodiments, the polymers will have a weight-average molecular weight of at least about 10,000 Daltons.

It should be noted that the polymers of Table 1 were all made using one precursor having an $R^1$ structure and one precursor having an $R^2$ structure, but a mixture of dithiol precursors may be used, if desired, as noted in reaction scheme (1). A plurality of dithiol precursors may be used to make a copolymer or terpolymer, or any degree of mixed polymer. The mixed polymer may be a block mixed polymer, such as a block copolymer having the general formula:

(B)

where each instance of $R^3$ is independently an organic or hetero-organic group different from $R^1$, and each instance of $R^3$ may be the same species. As above in structure (A), each instance of $R^1$ is independently an organic or hetero-organic group, each instance of $R^1$ may be the same species, each instance of $R^2$ is independently an organic or hetero-organic group that may have a molecular weight of not more than about 120 Daltons, each instance of $R^2$ may be the same species, and m and n are each integers greater than or equal to 1. The polymer (B) may also be reacted with a thiol-reactive precursor containing the species X, and optionally a thiol-reactive precursor containing the species Z, to attach X and/or Z to the polymer (B) as with the polymer (A) above. The result would be a polymer having the general formula:

(C)

with $R^1$, $R^2$, $R^3$, m, n, X, and Z defined as described above. To make a block copolymer such as the polymer (B) or the polymer (C), a first segment is made by reacting a 1,3,5 substituted HT having the general formula with a first dithiol precursor $HSR^1SH$, optionally using a solvent, either to extinction of the first dithiol precursor or to a desired stopping point. If a portion of the first dithiol precursor remains after reaching the stopping point, the remainder of the first dithiol precursor may be removed, or the first segment may be removed from the reaction mixture. A second segment is made by reacting the 1,3,5 substituted HT with a second dithiol precursor $HSR^3SH$ by a similar procedure, with $R^1$, $R^2$, and $R^3$ defined as above. The first and second segments are then mixed together with the 1,3,5 substituted HT precursor to encourage formation of a block copolymer. A solvent may be used to control viscosity of the polymerization mixture, if desired. A random copolymer may be made by mixing together the first and second dithiol precursors, optionally with a solvent, and adding the 1,3,5 substituted HT, with mild heat, to form a polymer.

It should also be noted that more than one triazine precursor may be used to make a polymer. A random copolymer may be made by using two different triazine precursors with one dithiol precursor. A block copolymer may be made by making a first segment using a first triazine precursor, making a second segment using a second triazine precursor, and then joining the first and second segments using the first triazine precursor, the second triazine precursor, or a mixture of the first and second triazine precursors. Further mixed polymers may be made by using mixtures of dithiol precursors and mixtures of triazine precursors.

In the formulas herein, X and Z may be any thiol reactive species. Of particular use, X and/or Z may be a therapeutic agent for treating a medical condition. X and/or Z may be a species selected from the group consisting of hydrogen, an alkane thiol, an aromatic thiol such as a thiophenol or a thioaniline, a peptide, a protein, a thio-acid, a nucleotide, and combinations thereof, with the proviso that X and Z are not both hydrogen. X and/or Z may be a reactive or non-reactive species, a cargo, a linking group, a drug, a functional species for further modification after construction of the polymer (A) or the polymer (B), a polymerization starter, a chemical species capable of initiating depolymerization, or a combination thereof. Any of the above species may be a linking species or group, or a non-linking species or group.

When X is a linking group, the following structure may result:

(D)

where K is any species bondable to X, and $R^1$, $R^2$, and n are defined as above. Z may also be a linking group, which may be the same as or different from X, in which case a K group may also be bonded to Z. K may be another polythioaminal segment that links to X via thiol reactivity, as X is linked to the polythioaminal product of reaction (2), or K may be any other desired species, for example another polymer, peptide, reactive or non-reactive species, cargo, linking group, functional species, polymerization starter, or depolymerization starter that links to X via any suitable linkage. K may also be a species selected from the group consisting of hydrogen, an alkane thiol, an aromatic thiol such as a thiophenol or a thioaniline, a peptide, a protein, a thio-acid, a nucleotide, and combinations thereof.

X and Z may each come from a solid, a liquid, or a gas. In reaction (1) above, the reaction with HS—X may be performed in a bulk liquid phase or at a phase interface between the bulk liquid and a gas phase, an immiscible liquid phase, or a solid phase. Also in reaction (1) above, the reaction with HS—X may be performed in a bulk liquid phase or at a phase interface between the bulk liquid and a gas phase, an immiscible liquid phase, or a solid phase.

Figure 3:
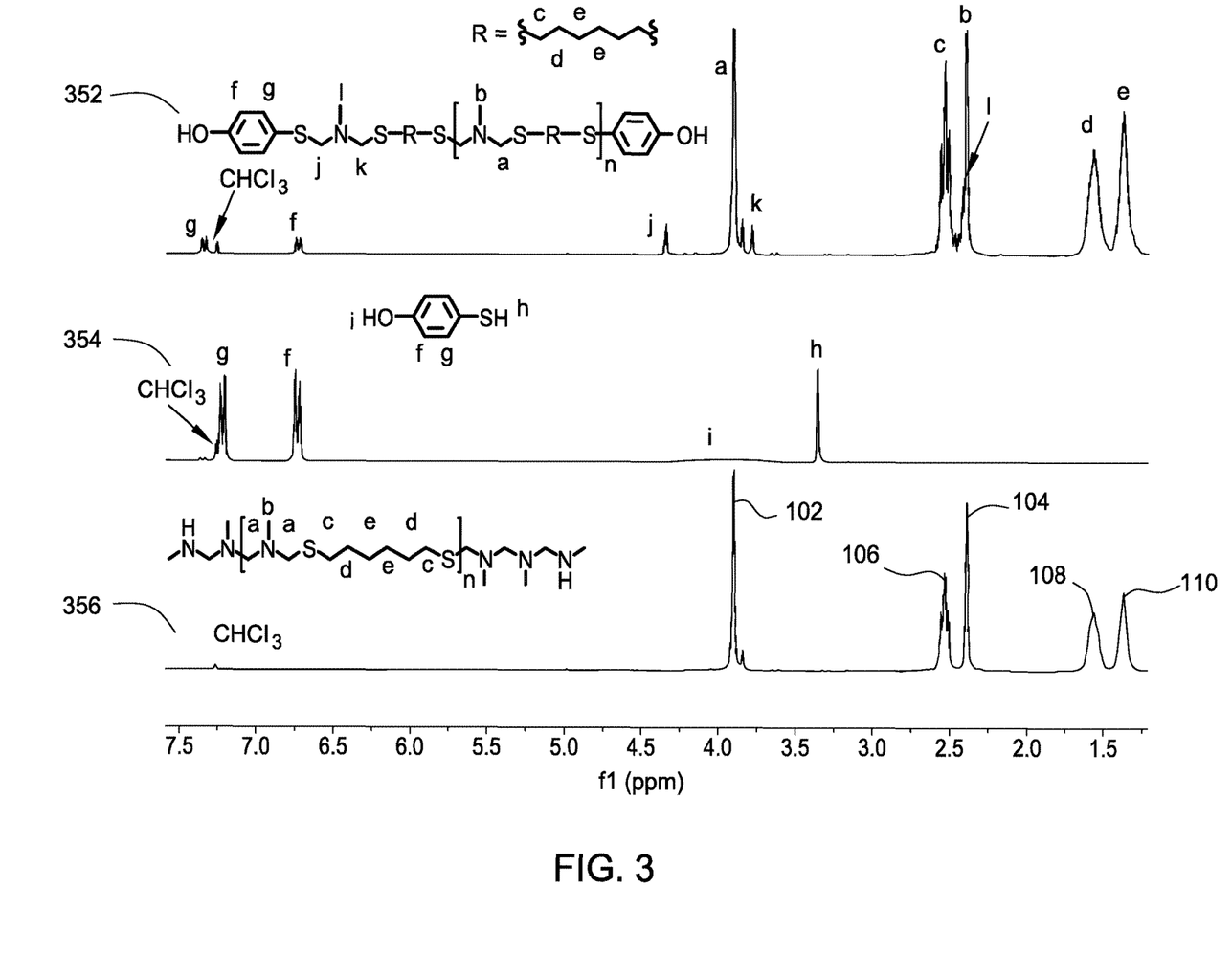
FIG. 3 is a composite of 1H-NMR traces of the product of the reaction of FIG. 1, the 1H-NMR trace of thiophenol, and the 1H-NMR trace of the product obtained by reacting the product of the reaction of FIG. 1 with thiophenol.

FIG. 3 is a composite of 1H-NMR traces of the reaction product 352 between polymer 1a above and thiophenol, the 1H-NMR trace of thiophenol 354, and the 1H-NMR trace of the polymer 1a 356. Peaks 102, 104, 106, 108, and 110 are visible in trace 356 indicating the structure of polymer 1a, as described above in connection with FIG. 1. Peaks 304 and 306 in the traces 352, 356 indicate aromatic carbon atoms in the phenyl ring. Peak 302 of trace 354, which is not visible in the traces 352, 356, indicates a new linkage at the carbon atom in the alpha position with respect to nitrogen and in the alpha position with respect to the sulfur atom bonded to the phenyl ring.

A nucleotide useable as the sulfur-bonded group X and/or Z may be a thiol modified oligonucleotide, as in either of the following:

Other species of interest for forming the sulfur-bonded groups X and/or Z include and the protein known as RANTES or chemokine ligand 5.

Polymer properties may be tuned by selecting the $R^1$ and $R^2$ groups. In particular, interaction of the polymer with water may be tuned by providing various hydrophilic and/or hydrophobic substituents. By using a large hydrophilic dithiol and a small hydrophobic substituted HT, a water-soluble polythioaminal may be made. For example, polymer 4a above was found to reduce in molecular weight to an $M_n$ below about 4,500 after 4 days in a water solution. Slow degradation of such a polymer into non-toxic PEG components provides the potential for therapeutic delivery agents that do not have toxic effects.

Figure 4:
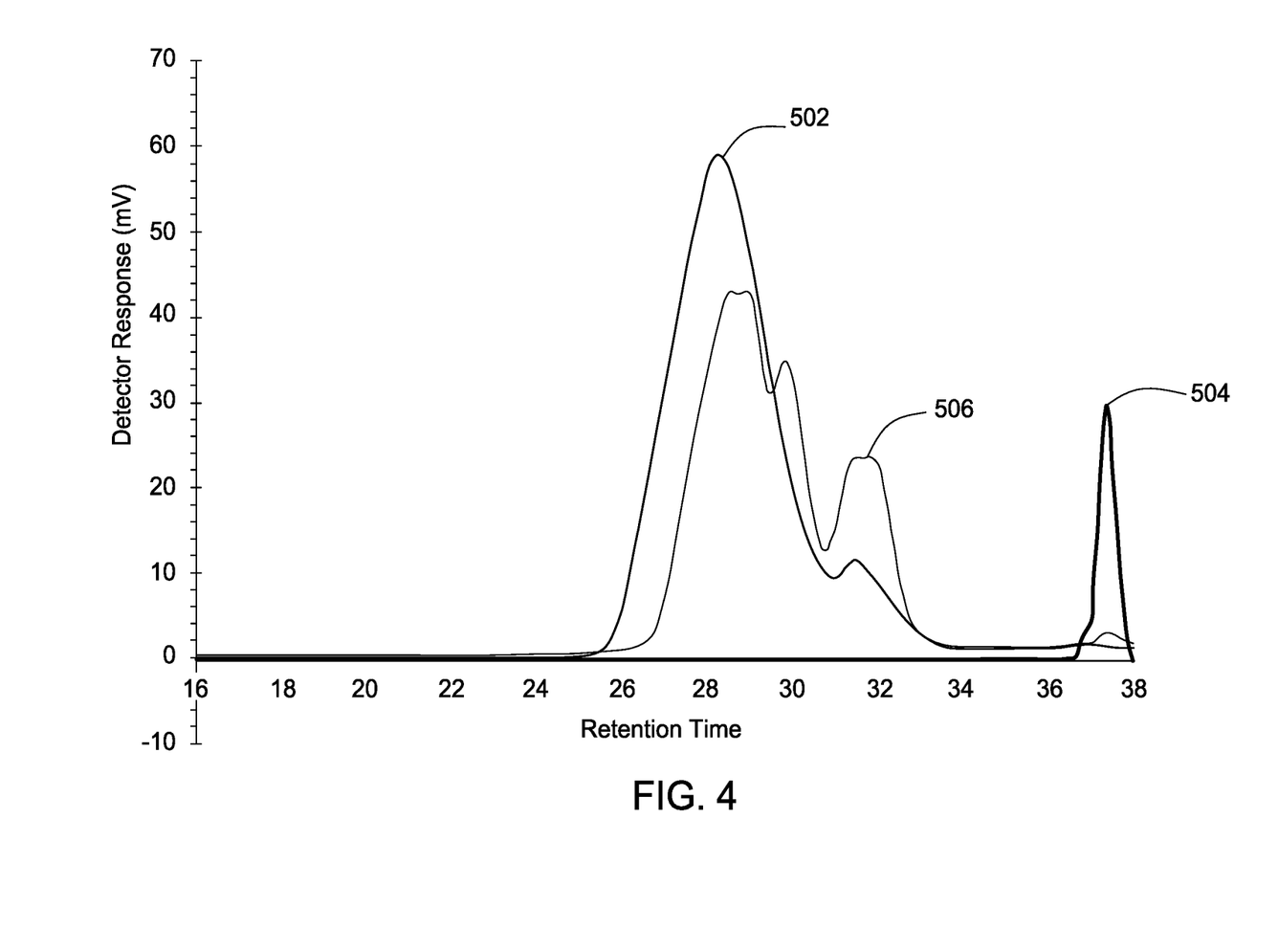
FIG. 4 is a GPC trace showing the trace of a polymer, a peptide, and the product of a reaction between the polymer and the peptide.

In one example, the thiol-containing amphiphilic alpha-helical peptide SEQ. ID: NO: 1-$NH_2$ was attached to water-soluble polythioaminal polymer 4a by mixing the peptide and polymer under mild heating. Initially, the peptide was observed to form a white powder phase in the viscous polymer. Maintaining the reaction mixture at 85° C. for 8 hours produced a single phase polymer-peptide product. FIG. 4 is a GPC trace showing the trace of the starting polymer 4a 502, the starting peptide SEQ. ID: NO: 1-$NH_2$ 504, and the polymer-peptide product 506. The GPC trace of the polymer-peptide product 506 shows the effect of different numbers of repeating polythioaminal units attached to the peptide.

To investigate toxicity of the polymer-peptide product, the polymer-peptide product was dissolved in a simulated physiological environment comprising 10% prenatal bovine serum in a phosphate-buffered saline solution. No precipitation or aggregation was observed in the solution over 24 hours. The polymer-peptide products was also incubated with human embryonic kidney cells from cell line HEK293 for 24 hours, after which more than 90% cell viability was observed. No hemolysis was observed at doses up to 1000 mg/L. In contrast, viability of the HEK293 cells in the presence of the peptide alone was below 70% at a dose of 50 mg/L, while viability after similar incubation period with the polymer-peptide product was more than 80% at 200 mg/L.

A method of forming a material includes mixing an N-substituted hexahydrotriazine and a dithiol in a vessel to form a first mixture, and heating the first mixture to form a polythioaminal polymer. The substituent bonded to a nitrogen atom of the N-substituted hexahydrotriazine forms a hydride byproduct during polymerization. The substituent is selected such that the hydride byproduct is volatile at temperatures up to about 200° C. so that the hydride byproduct can be removed during polymerization to increase molecular weight of the polymer.

The method may further comprise adding a thiol-reactive material to the polythioaminal polymer to form a second mixture, and the second mixture may be heated to form an end-modified polythioaminal polymer, which may be a therapeutic agent. A solvent may be added to the N-substituted hexahydrotriazine or the dithiol prior to forming the first mixture, may be added during forming the first mixture, may be added to the first mixture after forming the first mixture, or may be added to the second mixture after forming the second mixture.

The first mixture may be heated to a temperature generally above room temperature and up to about 200° C. In some cases, temperatures above 200° C. may be used, but some polymers degrade at temperatures above 200° C. In most cases, a reaction temperature of 50-100° C., for example about 80° C., will promote reaction to form the polythioaminal polymer. The first mixture may be stirred, or otherwise mixed, while forming the polythioaminal polymer.

A higher reaction temperature may be used in some cases to promote removal of byproducts during the reaction. The hexahydrotriazine precursor may be any of the hexahydrotriazine precursors described herein, and hydrogen atoms bonded to any or all nitrogen atoms in each hexahydrotriazine molecule may be substituted. One or more of the substituents bound to the nitrogen atoms of the hexahydrotriazine precursor will form a hydride byproduct during the polymerization reaction, so the substituent is generally chosen to form a hydride byproduct that is volatile at temperatures up to 200° C. The byproduct may volatilize from heating alone, or vacuum may be applied to encourage volatility of the byproduct. For at least this reason, higher temperatures may promote development of higher molecular weight in the polymer through removal of byproducts.

Formation of the polymer may be controlled to any desired degree by adjusting temperature of the reaction mixture and by adjusting solvent content. Lowering temperature, or adding solvent, will slow the growth of the molecular weight. Raising temperature, or using less solvent, will promote growth of molecular weight, up to a point. If the reaction mixture is stirred or mixed, high viscosity may make mixing, and subsequent processing, difficult. Solvents such as N-methyl-2-pyrrollidone or other suitable aprotic solvents, which may include dimethylsulfoxide (DMSO), N,N-dimethylformamide (DMF), N,N-dimethylacetamide (DMA), Propylene carbonate (PC), and propylene glycol methyl ether acetate (PGMEA), of which any mixture may also be used.

The thiol-reactive material may include a species that is a reactive species, a non-reactive species, a cargo, a linking group, a drug, a functional species for further modification after construction of the end-modified polythioaminal polymer, a polymerization starter, a chemical species capable of initiating depolymerization, or a combination thereof. Some species that may be attached to a polythioaminal through a thiol-reactive material include alkane thiols, aromatic thiols such as a thiophenol or a thioaniline, peptides, proteins, thio-acids, nucleotides, and combinations thereof. The thiol-reactive material may be a solid, liquid or gas, and the reaction between the thiol-reactive material may take place entirely in the liquid phase or at an interface between solid and liquid or liquid and gas.

The methods described herein may be used to form a polymer comprising a repeating unit with the following structure:

and a segment with the following structure:

wherein $R^1$ is independently an organic or hetero-organic species, each instance of $R^2$ is independently a substituent having molecular weight no more than about 120 Daltons, X is a linking group covalently bonded to a sulfur atom, and K is any radical suitable for bonding to X. X may be a species selected from the group consisting of hexyl, dihydroxybutyl, and polyethylene glycol. The polymer may further comprise a segment with the following structure:

wherein Z is a species selected from the group consisting of a cargo, a drug, a chemical species capable of initiating depolymerization, or a combination thereof. Z may be a species selected from the group consisting of an alkane thiol, an aromatic thiol, a peptide, a thio-acid, a nucleotide, and combinations thereof. Z may be a therapeutic agent. In the structure above, the wavy lines denote a covalent chemical bond to a species or radical not shown in the structure.

While the foregoing is directed to embodiments of the present invention, other and further embodiments of the invention may be devised without departing from the basic scope thereof, and the scope thereof is determined by the claims that follow.

What is claimed is:

1. A method of preparing a polymer material, comprising:
mixing an N-substituted hexahydrotriazine with a dithiol to form a first mixture, the N-substituted hexahydrotriazine having the structure wherein each $R^2$ is independently a hydrogen, a fluorine, an alkyl substituent, a cycloalkyl substituent, or an aromatic substituent, wherein each $R^2$ has a molecular weight no more than 120 Daltons,
the dithiol having the structure wherein $R^1$ is a hydrocarbon species, an aromatic species, a polyol species, or a polyether species; and
heating the first mixture to form a product mixture comprising a polythioaminal polymer.

2. The method of claim 1, comprising adding a thiol-reactive material to the polythioaminal polymer to form a second mixture, and heating the second mixture to form a second product mixture comprising a modified polythioaminal polymer.

3. The method of claim 2, wherein the thiol-reactive material comprises a species selected from the group consisting of a hydrogen, an alkane thiol, an aromatic thiol, a peptide, a thio-acid, a nucleotide, and combinations thereof.

4. The method of claim 1, comprising adding a solvent to the N-substituted hexahydrotriazine prior to mixing with the dithiol.

5. The method of claim 1, wherein the polythioaminal polymer is represented by wherein:
each $R^1$ is independently a hydrocarbon species, an aromatic species, a polyol species, or a polyether species,
each $R^2$ is independently a hydrogen, a fluorine, an alkyl substituent, a cycloalkyl substituent, or an aromatic substituent, wherein each $R^2$ has a molecular weight no more than 120 Daltons,
X is selected from the group consisting of a hydrogen, an alkane thiol, an aromatic thiol, a peptide, a thio-acid, a nucleotide, and combinations thereof,
Z is selected from the group consisting of a hydrogen, an alkane thiol, an aromatic thiol, a peptide, a thio-acid, a nucleotide, and combinations thereof,
at least one of X and Z is not hydrogen, and
n is an integer greater than or equal to 1.

6. The method of claim 5, wherein X includes a thiol-modified oligonucleotide, a thiol-containing organic acid, or SEQ. ID NO: 1-NH$_2$.

7. The method of claim 5, wherein X is a peptide species.

8. The method of claim 7, wherein at least one instance of $R^1$ is polyethylene glycol.

9. The method of claim 5, wherein each instance of $R^2$ is a methyl group.

10. A method of preparing a polymer material, comprising:
mixing an N-substituted hexahydrotriazine with a dithiol to form a first mixture; and
heating the first mixture to form a product mixture comprising a polythioaminal polymer, the polythioaminal polymer represented by wherein:
each $R^1$ is independently a hydrocarbon species, an aromatic species, a polyol species, or a polyether species,
each $R^2$ is independently a hydrogen, a fluorine, an alkyl substituent, a cycloalkyl substituent, or an aromatic substituent, wherein each $R^2$ has a molecular weight no more than 120 Daltons,
X is selected from the group consisting of a hydrogen, an alkane thiol, an aromatic thiol, a peptide, a thio-acid, a nucleotide, and combinations thereof,
Z is selected from the group consisting of a hydrogen, an alkane thiol, an aromatic thiol, a peptide, a thio-acid, a nucleotide, and combinations thereof,
at least one of X and Z is not hydrogen, and
n is an integer greater than or equal to 1.

11. The method of claim 10, wherein X includes a thiol-modified oligonucleotide, a thiol-containing organic acid, or SEQ. ID NO: 1-NH$_2$.

12. A method of preparing a polymer material, comprising:
mixing an N-substituted hexahydrotriazine with a dithiol to form a first mixture, wherein a substituent bonded to one or more nitrogen atoms of the N-substituted hexahydrotriazine forms a hydride that is volatile at temperatures less than 200° C.; and
heating the first mixture to form a product mixture comprising a polythioaminal polymer, the polythioaminal polymer represented by and a segment represented by wherein:
$R^1$ is independently a hydrocarbon species, an aromatic species, a polyol species, or a polyether species,
each $R^2$ is independently a hydrogen, a fluorine, an alkyl substituent, a cycloalkyl substituent, or an aromatic substituent, wherein each $R^2$ has a molecular weight no more than 120 Daltons, X is a linking group selected from the group consisting of hexyl, dihydroxybutyl, and polyethylene glycol, K is selected from the group consisting of hydrogen, an alkane thiol, an aromatic thiol, a peptide, a protein, a thio-acid, a nucleotide, and combinations thereof, and the wavy bond represents a bond to another atom in the chemical structure.

13. The method of claim 12, comprising a segment represented by wherein:

Z is selected from the group consisting of a hydrogen, an alkane thiol, an aromatic thiol, a peptide, a thio-acid, a nucleotide, and combinations thereof, and the wavy bond represents a bond to another atom in the chemical structure.

14. The method of claim 12, wherein the polymer has a weight-average molecular weight of at least 10,000 Daltons.

15. The method of claim 2, further comprising removing volatile byproducts from the first product mixture, the second product mixture, or a combination thereof.

16. The method of claim 10, further comprising removing volatile byproducts from the product mixture.

17. The method of claim 12, further comprising removing volatile byproducts from the product mixture.

* * * * *